(12) United States Patent
Creecy et al.

(10) Patent No.: US 8,945,894 B2
(45) Date of Patent: Feb. 3, 2015

(54) ALTERNATING ELECTRIC CURRENT DIRECTS, ENHANCES, AND ACCELERATES MESENCHYMAL STEM CELL DIFFERENTIATION INTO EITHER OSTEOBLASTS OR CHONDROCYTES BUT NOT ADIPOCYTES

(71) Applicants: Courtney M. Creecy, San Antonio, TX (US); Rena Bizios, San Antonio, TX (US)

(72) Inventors: Courtney M. Creecy, San Antonio, TX (US); Rena Bizios, San Antonio, TX (US)

( * ) Notice: Subject to any disclaimer, the term of this patent is extended or adjusted under 35 U.S.C. 154(b) by 0 days.

(21) Appl. No.: 13/630,882

(22) Filed: Sep. 28, 2012

(65) Prior Publication Data
US 2013/0089908 A1    Apr. 11, 2013

Related U.S. Application Data

(60) Provisional application No. 61/540,432, filed on Sep. 28, 2011.

(51) Int. Cl.
*C12N 13/00* (2006.01)
*C12M 1/42* (2006.01)
*C12N 5/0775* (2010.01)

(52) U.S. Cl.
CPC .............. *C12N 13/00* (2013.01); *C12M 35/02* (2013.01); *C12N 5/0663* (2013.01); *C12N 2529/00* (2013.01); *C12N 2533/54* (2013.01)
USPC ......... 435/173.1; 435/325; 435/377; 435/383

(58) Field of Classification Search
USPC ................ 435/173.1, 325, 377, 383
See application file for complete search history.

(56) References Cited

U.S. PATENT DOCUMENTS

| | | |
|---|---|---|
| 2006/0057693 A1 | 3/2006 | Simon |
| 2008/0039901 A1 | 2/2008 | Kronberg et al. |
| 2008/0227191 A1 | 9/2008 | Tsukada |
| 2008/0227202 A1 | 9/2008 | Dancu |
| 2009/0124013 A1 | 5/2009 | Kouns |
| 2010/0233142 A1 | 9/2010 | McLaughlin et al. |
| 2011/0034753 A1 | 2/2011 | Dobson et al. |

FOREIGN PATENT DOCUMENTS

WO    2005/059118 A2    6/2005

OTHER PUBLICATIONS

Reichert et al., "Fabrication of polycapolactone collagen hydrogel constructs seeded with mesenchymal stem cells for bone regeneration." (2009) Biomedical Materials, vol. 4: 065001 1-11.*
Harnett et al. "The surface energy of various biomaterials coated with adhesion molecules used in cell culture." (2007) Colloids and Surfaces B: Biointerfaces, vol. 55: 90-97.*
Hronik-Tupaj, Marie, et al; Osteoblastic Differentiation and Stress Response of Human Mesenchymal Stem Cells Exposed to Alternating Current Electric Fields; Biomedical Engineering Online; vol. 10, No. 1, Jan. 26, 2011.
European Patent Office; International Search Report and Written Opinion; PCT Application No. PCT/US2012/057961; Dec. 13, 2012.

* cited by examiner

*Primary Examiner* — Jon P Weber
*Assistant Examiner* — Teresa E Knight

(57) ABSTRACT

A method for directing, enhancing, and accelerating mesenchymal stem cell functions using alternating electric current. Mesenchymal stem cells are preferentially directed to either osteoblast or chondrocyte lineages, but not to the adipocyte lineage. when exposed to alternating electric current.

33 Claims, 6 Drawing Sheets

ALTERNATING ELECTRIC CURRENT DIRECTS, ENHANCES, AND ACCELERATES MESENCHYMAL STEM CELL DIFFERENTIATION INTO EITHER OSTEOBLASTS OR CHONDROCYTES BUT NOT ADIPOCYTES

This application claims priority. to U.S. Provisional Patent Application Ser. No. 61/540,432, filed Sep. 28, 2011, entitled "Alternating Electric Current Directs, Enhances, and Accelerates Mesenchymal Stem Cell Differentiation into Osteoblasts and Chondrocytes But Not Adipocytes," the entire contents of which are hereby incorporated by reference.

STATEMENT OF RIGHTS TO INVENTIONS MADE UNDER FEDERALLY SPONSORED RESEARCH

This invention was made in part during work supported by a grant from the Norman Hackman Advance Research Program (Texas), Grant Number BIOM-ARP 010115-0074-2007 with Rena Bizios as the Principal Investigator. The government may have certain rights in the invention.

FIELD OF THE INVENTION

The present invention relates generally to directing, enhancing, and accelerating mesenchymal stem cell functions using electrical stimuli, and more specifically to the use of electrical stimulus patterns and regimes to direct, enhance, and accelerate the differentiation of mesenchymal stem cells into specific cell types.

BACKGROUND

Mesenchymal stem cells are pluripotent bone marrow cells with the potential to differentiate into osteoblasts (bone cells), chondrocytes (cartilage cells), and adipocytes (fat tissue cells) upon appropriate stimulation. Understanding and utilizing the knowledge of how various stimuli direct, enhance, and accelerate the differentiation of stem cells is important for tissue engineering and regenerative medicine applications that require either new bone or new cartilage.

Conventionally, chemical stimuli (i.e., growth factors) have been used to promote stem cell differentiation along various pathways.

To date, the use of alternating electric current stimulation has not been explored as a means of directing. enhancing, and accelerating the differentiation of mesenchymal stem cells specifically to either osteoblasts or chondrocytes (but not to adipocytes). The research findings in the present disclosure show for the first time that certain electrical stimulus patterns and regimes direct. enhance, and accelerate differentiation of mesenchymal cells along specific pathways, namely to either osteoblasts (bone cells) or chondrocytes (cartilage cells), but not to adipocytes (fat tissue cells).

Electrical stimulation patterns and regimes that direct, enhance, and accelerate the differentiation of mesenchymal stem cells into either osteoblasts or chondrocytes (but not adipocytes) provide a novel approach to obtain differentiated cells needed in tissue engineering and regenerative medicine applications and thus has the potential for major clinical impact. For example. the present invention could be used for bone and cartilage regeneration as follows: (i) mesenchymal stem cells could be isolated from a patient; (ii) said mesenchymal stem cells could then be expanded and differentiated into either bone or cartilage cells in vitro; and (iii) then be returned to the donor patient as differentiated cells for tissue regeneration in vivo.

SUMMARY

In one embodiment, the present invention provides a method for directing. enhancing, and accelerating the differentiation of mesenchymal stem cells. Mesenchymal stem cells are cultured within a three-dimensional, current-conducting matrix or scaffold. and exposed to alternating electric current. In this embodiment, the mesenchymal stem cells are preferentially directed to either osteoblast or chondrocyte lineages, but not to the adipocyte lineages.

In another embodiment, the present invention provides a method for directing, enhancing, and accelerating the differentiation of mesenchymal stem cells. Mesenchymal stem cells are cultured on a two-dimensional current-conducting substrate. and exposed to alternating electric current. In this embodiment, the mesenchymal stem cells are preferentially directed to either osteoblast or chondrocyte lineages, but not to the adipocyte lineages.

In another embodiment, the present invention comprises a laboratory setup to expose mesenchymal stem cells to alternating electric current in order to direct. enhance, and accelerate the differentiation of mesenchymal stem cells to either osteoblast or chondrocyte lineages, but not to the adipocyte lineage, as compared to that of the controls, that is, cells cultured under similar culture conditions but not exposed to alternating electric current.

BRIEF DESCRIPTION OF THE DRAWINGS

The following drawings form part of the present specification and are included to further demonstrate certain aspects of the present invention. The invention may be better understood b) reference to one or more of these drawings in combination with the detailed description of specific embodiments presented herein.

Figure 3:
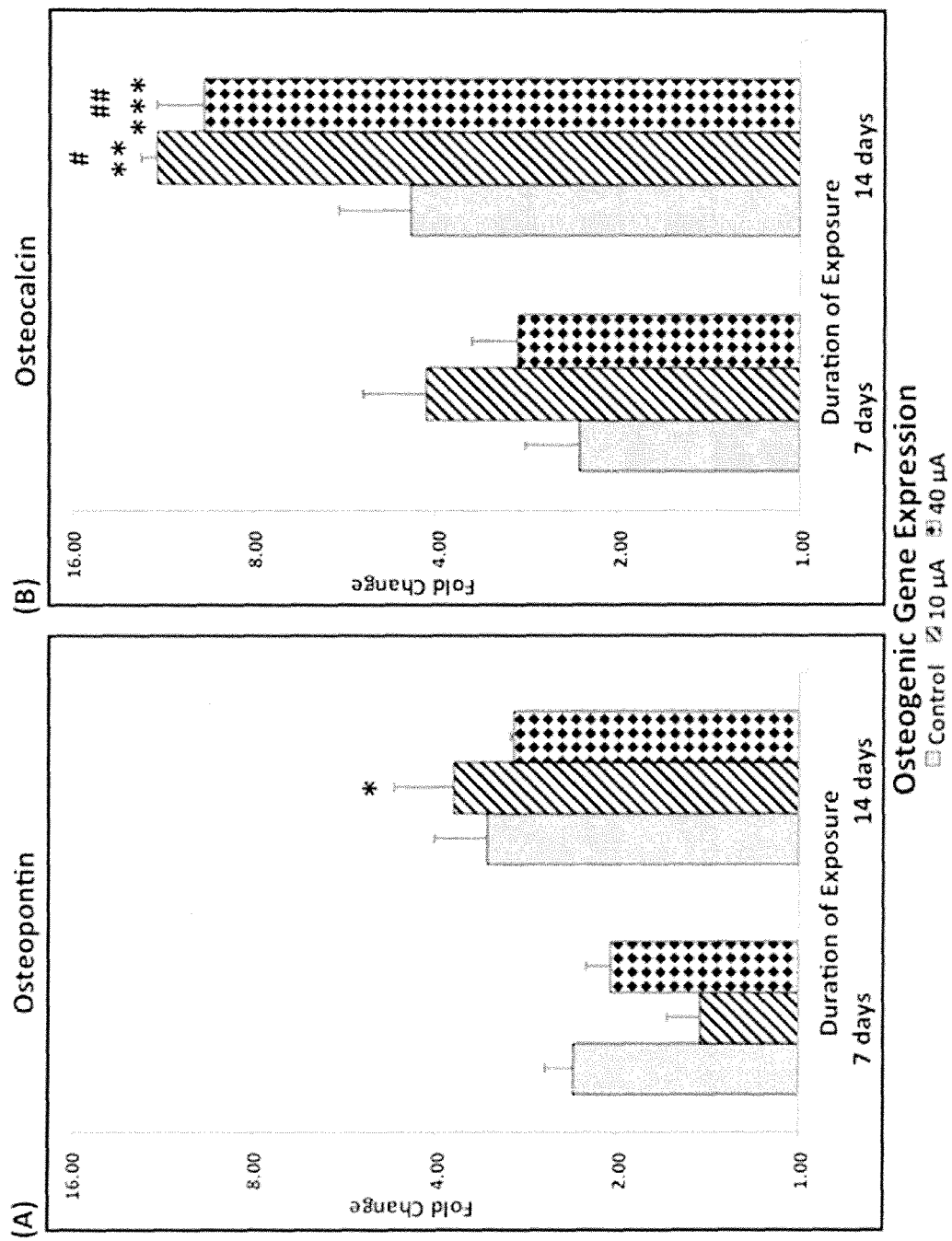

FIG. 3 is a graph showing that adult human mesenchymal stem cells cultured within type I collagen hydrogel constructs and exposed to alternating electric current for 6 hours daily for either 7 or 14 consecutive days express genes indicative of differentiation into the osteoblast phenotype. Osteopontin, a late-osteogenic gene, was significantly upregulated as a function of duration (14 versus 7 days) of exposure of MSCs to 10 µA alternating electric current (FIG. 3(A)). Compared to respective controls, osteocalcin (a late osteogenic gene) was significantly upregulated after the mesenchymal stem cells were exposed to either 10 µA (striped bars) or 40 µA (dotted bars) of alternating electric current for 14 days (FIG. 3(B)). Controls were MSCs cultured under similar conditions and time periods but not exposed to alternating electric current. Osteocalcin was also significantly unregulated as a function of duration (14 vs. 7 days) when MSCs were exposed to either 10 µA or 40 µA (FIG. 3(B)). Data are values±standard error of the mean. # $p<0.05$ (ANOVA and Tukey's test: osteocalcin results obtained under 10 µA compared to results obtained under from the respective control at day 14). n=4. ## $p<0.05$ (ANOVA and Tukey's test; osteocalcin results obtained from MSCs under 40 µA were compared to results obtained from the respective control at day 14). n=4. * $p<0.05$ (ANOVA and Tukey's test; osteopontin results obtained from MSCs under 10 µA at day 14 versus day 7). n=4  $p<0.05$ (ANOVA and Tukey's test; osteocalcin results obtained from MSCs under 10 µA at day 14 versus day 7). n=4* $p<0.05$ (ANOVA and Tukey's test; osteocalcin results obtained from MSCs under 40 µA at day 14 versus day 7).

Figure 4:
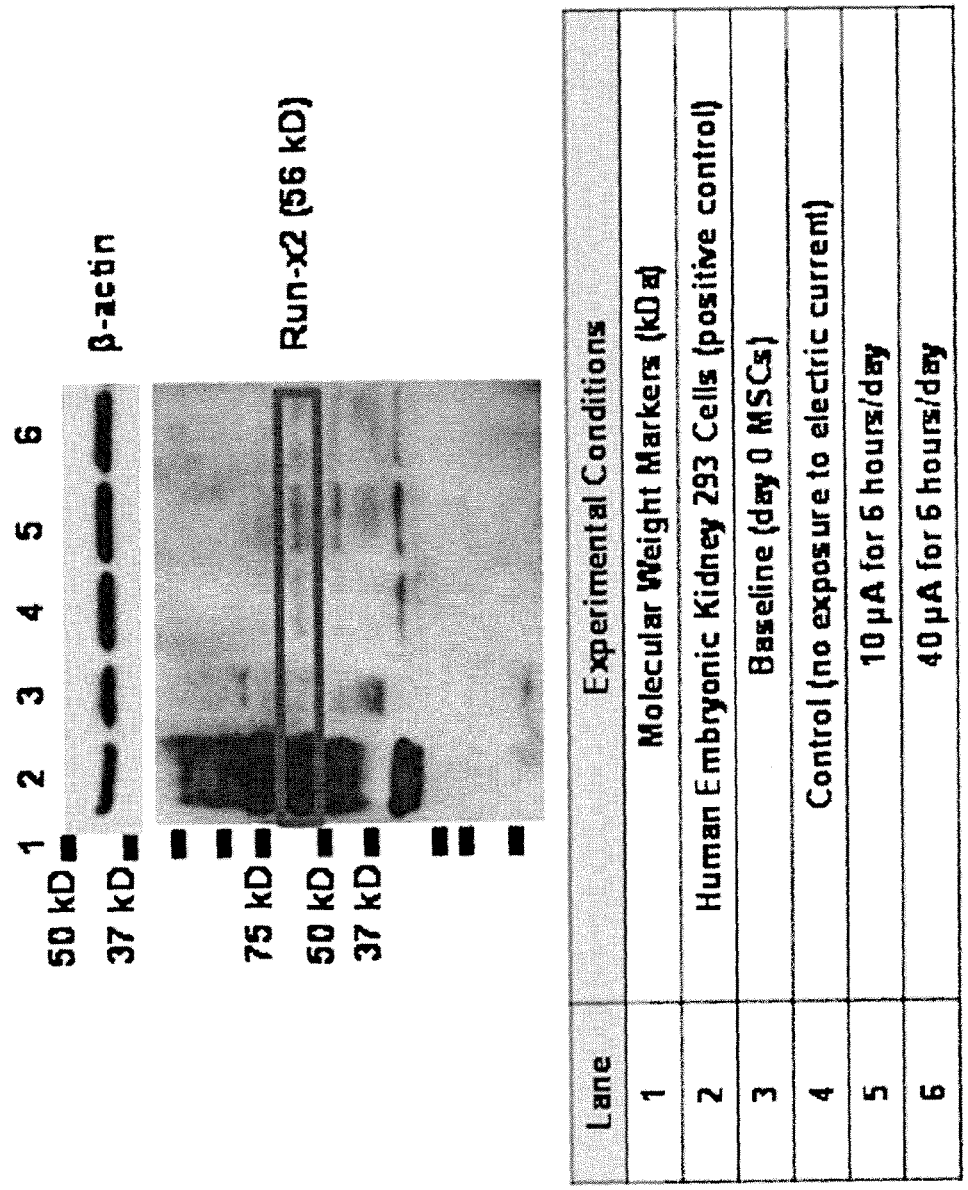

FIG. 4 depicts results of a Western blot showing Runx-2 protein production in adult human mesenchymal stem cells cultured on two-dimensional. ITO-coated glass after exposure to alternating electric current for 6 hours daily for 7 consecutive days. Adult human mesenchymal stem cells cultured on two-dimensional, ITO-coated glass and exposed to a 10 alternating electric current (lane 5) for 7 consecutive days exhibited higher expression of Runx-2 as compared to controls (lane 4). that is, cells cultured under similar conditions but not exposed to alternating electric current. MSCs exposed to 40 µA alternating electric current (lane 6) showed similar expression of Runx-2 as controls (lane 4), n=1.

Figure 5:
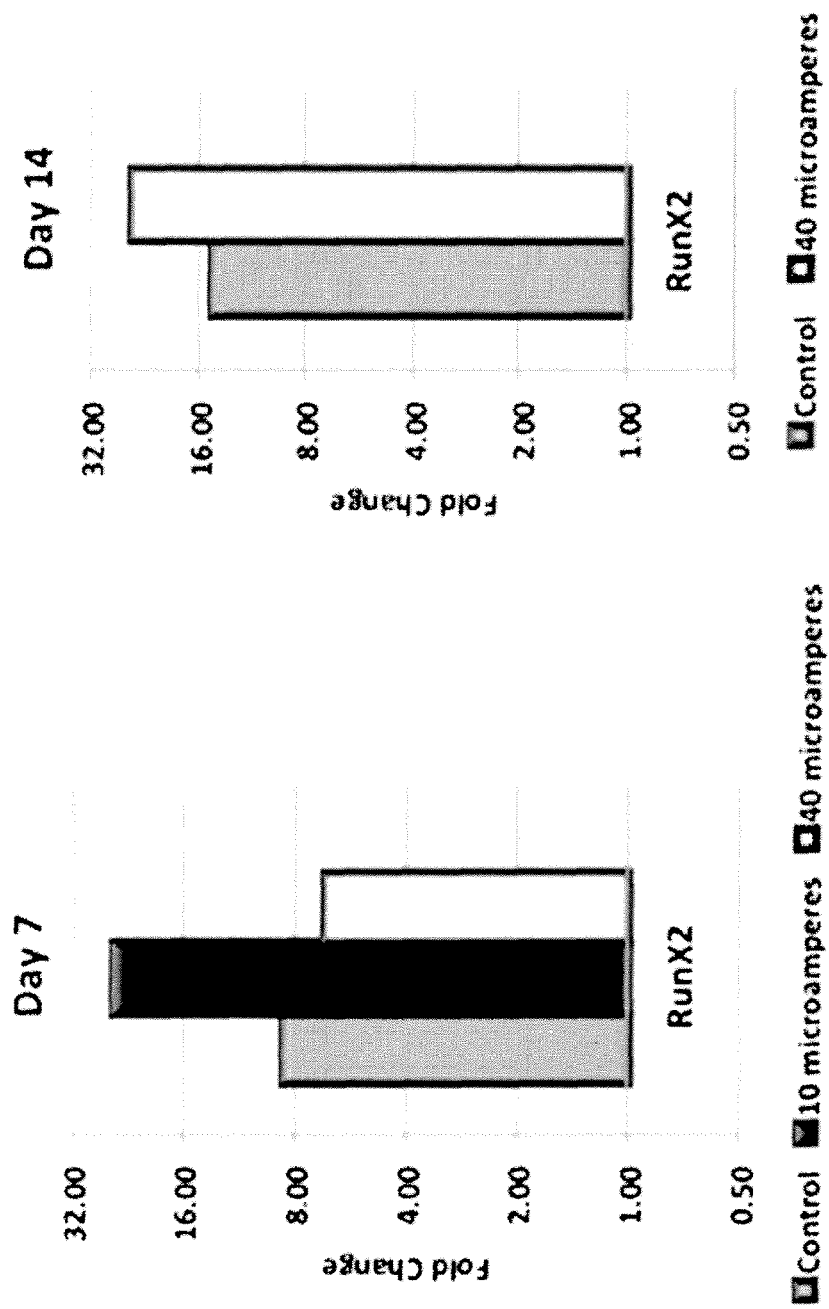

FIG. 5 is a graph showing early-osteoblast gene expression from adult human mesenchymal stem cells cultured on two-dimensional. ITO-coated glass after exposure to alternating electric current for 6 hours daily for either 7 or 14 consecutive days. Specifically. exposure of MSCs to 10 µA alternating electric current for 6 hours per day promoted increasing expression of Runx-2 (a pre-osteogenic gene pertinent to mesenchymal stem cell osteodifferentiation) as compared to the respective controls (i.e., MSCs not exposed to alternating electric current) after 7 consecutive days. Additionally, exposure of MSCs to 40 µA alternating electric current for 6 hours per day promoted increasing Runx-2 expression as compared to respective controls after 14 consecutive days. Relative gene expression (fold change) was calculated as "fold increase" above the baseline (that is, MSCs cultured under standard cell culture conditions in the absence of alternating electric current and analyzed at day 0. the day these MSCs were seeded), n=1.

Figure 6:
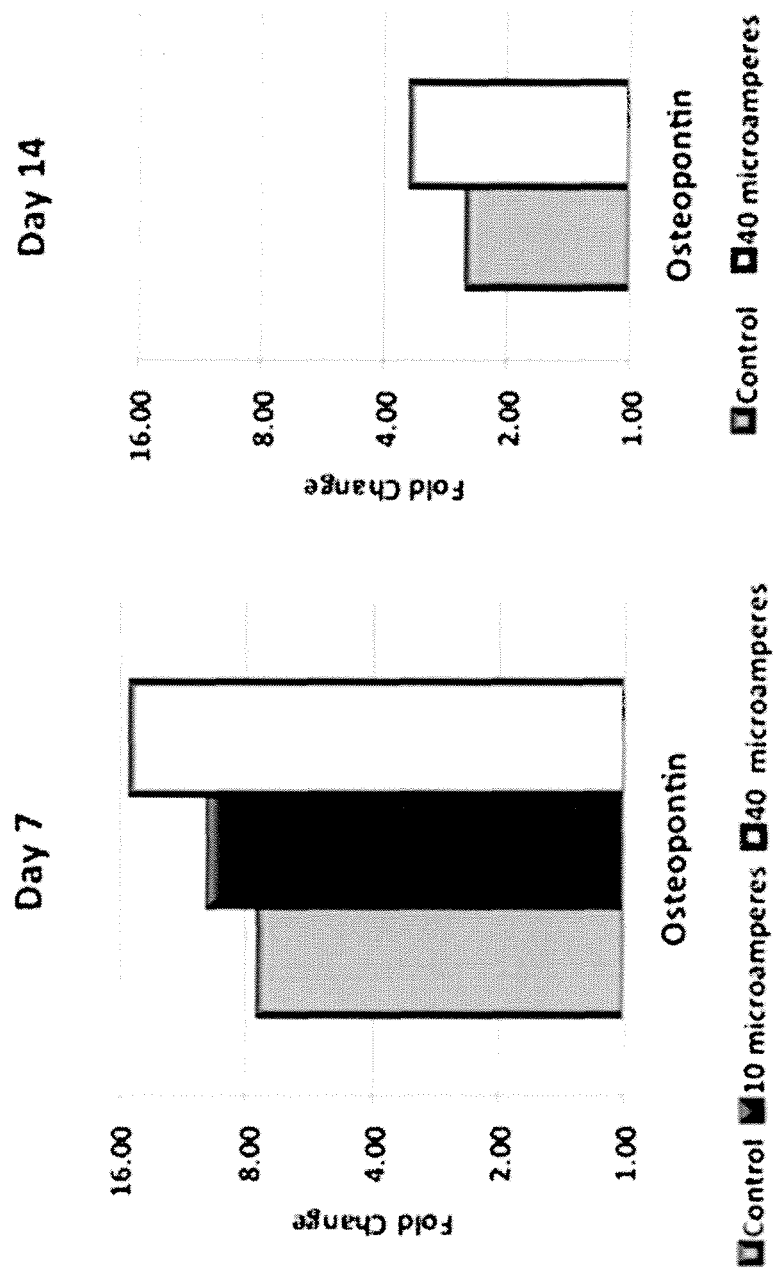

FIG. 6 is a graph show late-osteoblast gene expression of human adult mesenchymal stem cells cultured on a two-dimensional ITO-coated glass after exposure to alternating electric current for 6 hours daily for either 7 or 14 consecutive days. Specifically, exposure of MSCs to either 10 µA or 40 µA alternating electric current for 6 hours per day promoted increasing expression of osteopontin (a late-osteoblast genes pertinent to mesenchymal stem cell osteodifferentiation) as compared to respective controls (i.e., MSCs not exposed to electric stimulation) after 7 consecutive days. Moreover, exposure of MSCs to 40 µA alternating electric current for 6 hours per day promoted increasing osteopontin expression as compared to respective controls after 14 consecutive days. Relative gene expression (fold change) was calculated as "fold increase" above the baseline (that is, MSCs cultured under standard cell culture conditions in the absence of alternating electric current and analyzed at day 0, the day these MSCs were seeded), n=1.

DETAILED DESCRIPTION

The present invention relates generally to directing, enhancing, and accelerating mesenchymal stem cell functions using appropriate stimuli, and more specifically to the use of alternating electric current patterns and regimes to direct, enhance, and accelerate the differentiation of mesenchymal stem cells.

In one embodiment, the present invention provides a method for directing. enhancing, and accelerating the differentiation of mesenchymal stem cells. Mesenchymal stem cells are cultured on a two-dimensional, current-conducting substrate, for example a two-dimensional indium tin oxide-coated glass substrate, and exposed to alternating electric-current. The alternating electric current may consist of, but is not limited to, the following features: (i) alternating electric current of either 10 or 40 µA; (ii) frequency of 10 Hz; (iii) sinusoidal waveform; and (iv) duration of 6 hours per day for up to 28 consecutive days. In this embodiment, the mesenchymal stem cells are preferentially directed to either the osteoblast or chondrocyte lineages, but not to the adipocyte lineage, as compared to controls, that is, mesenchymal stem cells cultured under similar conditions but not exposed to alternating electric current.

In another embodiment, the present invention provides another method for directing, enhancing, and accelerating the differentiation of mesenchymal stem cells. Mesenchymal stem cells are cultured within a current-conducting, three-dimensional matrix or scaffold. for example a collagen hydrogel. and exposed to alternating electric-current. The alternating electric current may consist of, but is not limited to, the following features: (i) alternating electric current of either 10 or 40 µA; (ii) frequency of 10 Hz; (iii) sinusoidal waveform; and (iv) duration of 6 hours per day for up to 28 consecutive days. In this embodiment. the mesenchymal stem cells are preferentially directed to either the osteoblast or chondrocyte lineages, but not to the adipocyte lineage, as compared to controls, that is, mesenchymal stem cells cultured under similar conditions but not exposed to alternating electric current.

In one embodiment, mesenchymal stem cells are exposed to alternating electric current (for example 1-80 µA, 1-100 Hz, sinusoidal waveform) in vitro for 1-6 hours/day. In this embodiment, the differentiation of mesenchymal stem cells along one of two different lineages is enhanced: (i) osteoblasts cultured in three-dimensional. current-conducting matrices for up to 28 consecutive days; (ii) chondrocytes cultured on two-dimensional, current-conducting substrates for up to 28 consecutive days. In contrast, exposure to alternating electric current in this embodiment does not enhance the differentiation of mesenchymal stem cells into adipocytes. These results were determined in comparison to respective controls (that is, cells cultured under similar conditions but not exposed to alternating electric current).

In another embodiment, the present invention comprises an laboratory setup for directing, enhancing, and accelerating the differentiation of mesenchymal stem cells toward osteoblast and chondrocyte lineages, but not the adipocyte lineage, when compared with mesenchymal stem cells cultured under control (i.e., not exposed to alternating electric current) conditions. In this embodiment. the laboratory setup is comprised of a function generator, oscilloscope, multimeter, resistor, current-conducting base, current-conducting anode, a cathode substrate, and cell-culture chambers that are incorporated as part of an electric circuit. Incorporation of the cell-culture chambers as part of the electric circuit allows the mesenchymal stem cells contained within the cell-culture chambers to be exposed to alternating electric current for a specified duration and/or pattern of exposure in a sterile, 5% carbon dioxide/95% A air environment, at constant temperature (e.g., 37° C.).

In another embodiment, the invention comprises differentiated mesenchymal stem cells produced by the methods described herein.

Example 1

Standard Cell Culture Conditions

Unless otherwise noted. mesenchymal stem cells were cultured in mesenchymal stern cell growth media (as described in the Culture Medium for Human Mesenchymal Stem Cell Cultures section) under standard cell culture conditions (5% $CO_2$/95% air) in a sterile. humidified environment at 37° C.
Adult Human Mesenchymal Stem Cells (MSCs)

Cryopreserved adult human mesenchymal stem cells from normal human bone marrow were obtained commercially. These MSCs were characterized by the vendor ho provides evidence of the cell differentiation potential into osteogenic (as indicated by calcium mineralization), chondrogenic (as indicated by Type II collagen). and adipogenic (as indicated by neutral lipid) lineages. Specifically, these MSCs tested positive for CD105 (endoglin; SH2 marker), CD166 (ALCAM marker). CD29 (integrin 131 marker) and CD44 (HCAM marker), but negative for CD14, CD34 and CD45 (hematopoietic markers).
Culture Medium for Human Mesenchymal Stem Cell Cultures Adult human mesenchymal stem cells were cultured in mesenchymal stem cell growth medium that keeps the mesenchymal stem cells in the undifferentiated state under standard cell culture conditions for up to five cell passages. Mesenchymal stem cell growth medium consisted of mesenchymal stem cell basal-medium supplemented with fetal bovine serum, L-glutamine, and gentamicin/amphotericin-B (details regarding the respective concentrations of the supplements are not known because they are considered proprietary information by the vendor).

Example 2

Electric Current-Conductive Substrates for Culture of Human Mesenchymal Stem Cells Two types of electrically conductive substrates were used in this study for the in vitro culture of human bone cells and the exposure of these cells to alternating electric-current stimulation: (i) Indium Tin Oxide (ITO)-coated glass; and (ii) Type I collagen hydrogels. The following sections detail the synthesis and characterization of both these substrates.

Preparation of Two-Dimensional Indium Tin Oxide-Coated Glass

Aluminosilicate glass, coated with Indium Tin Oxide (ITO) on one side, was purchased commercially and prepared for cell culture as follows. Briefly, each substrate was cleaned by sonication sequentially for 5 minutes in each of the following chemicals: (i) hexane, (ii) methanol; and (iii) methylene chloride, washed in deionized water three times, allowed to dry, and sterilized (i.e., by autoclaving). The clean substrates were then coated with fibronectin overnight prior to use in experiments with mesenchymal stem cells.
Fabrication of Collagen Hydrogels High concentration (greater than 5 mg/mL) rat tail Type I collagen (dissolved in acetic acid) was commercially obtained. Collagen hydrogels were prepared according to the manufacturer's protocols to obtain final collagen concentrations between 2-8 mg/mL. The collagen hydrogels were maintained at 37° C. for approximately 30 minutes to achieve complete solidification of the hydrogels. At this time, mesenchymal stem cell growth medium was added to each chamber. All collagen hydrogels were maintained under sterile, standard cell culture conditions for up to 24 hours before use in experiments.
Fabrication of Cell-Containing Collagen Hydrogel Constructs Collagen hydrogel constructs were three-dimensional matrices or scaffolds composed of Type I collagen and contained adult human mesenchymal stem cells. To prepare such constructs, adult human mesenchymal stem cells were gently mixed (and, thus, dispersed) into the mesenchymal stem cell growth media prior to hydrogel solidification. These constructs were maintained under sterile, standard cell-culture conditions for at least 30 minutes to achieve complete solidification of the hydrogels. At that time, appropriate medium was added on top of each mesenchy mal stem cell-containing collagen hydrogel construct. All mesenchymal stem cell-containing collagen hydrogel constructs were maintained at standard cell culture conditions for 24 hours before use in experiments.

Example 3

Figure 1:
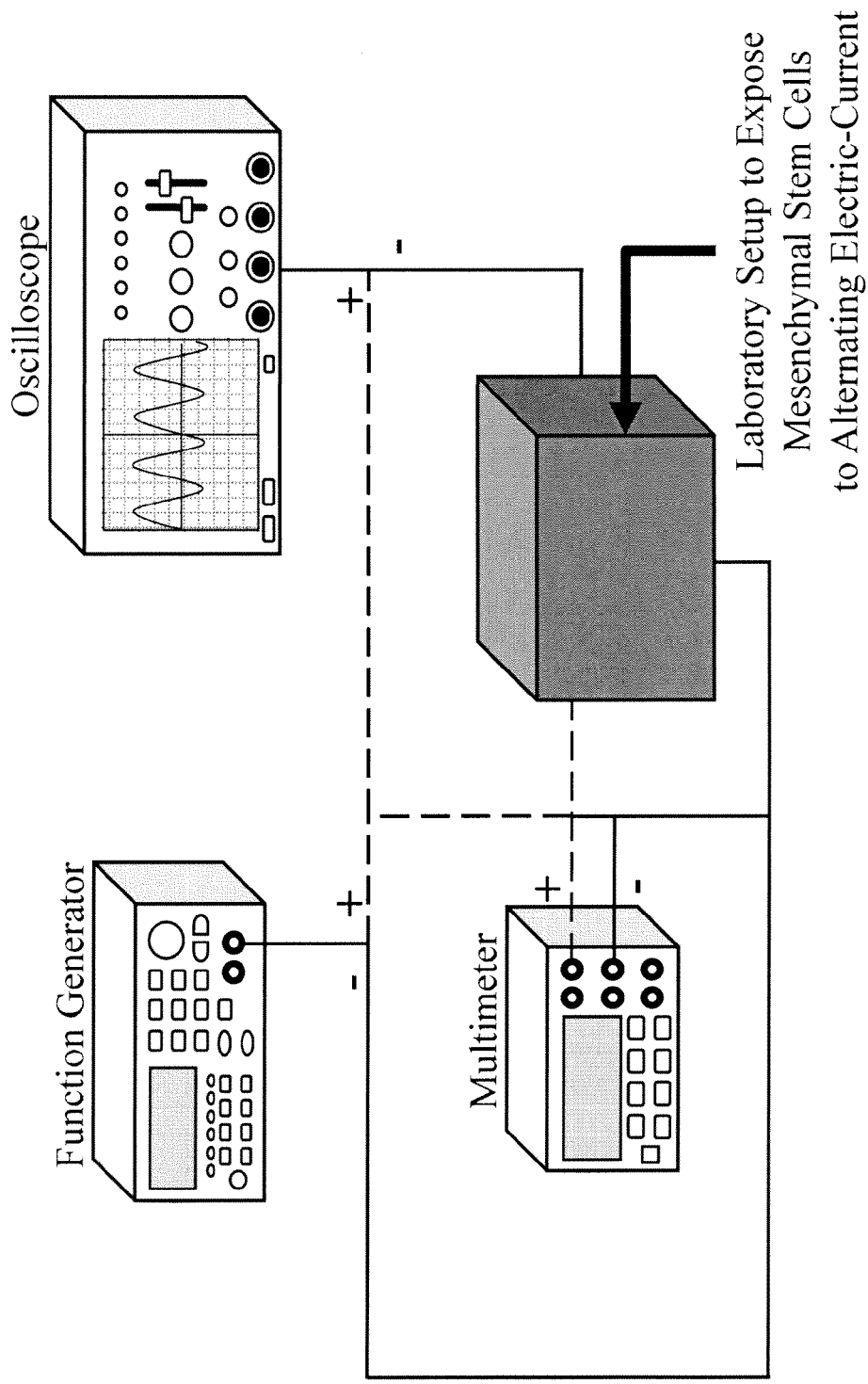
FIG. 1 is a schematic illustration (not to scale) of an alternating electric-current laboratory setup in accordance with the present invention. The set-up is comprised of a function generator, oscilloscope, multimeter. resistor, current-conducting base. cell-culture chamber, current-conducting anode, and a cathode substrate. The cell-containing chambers are incorporated in an electric circuit that allows exposure of mesenchymal stem cells to alternating electric current. Dashed lines represent positive electrical connections while solid lines represent negative electrical connections. The cell-culture chambers provide an environment that maintains: (1) sterile conditions; (2) constant temperature (e.g., 37° C.); and (3) reproducible, consistent exposure of mesenchymal stem cells to alternating electric current for the specified duration and/or pattern of exposure.

Exposure of Human Mesenchymal Stem Cells to Alternating Electric Current in Vitro Alternating Electric Current SystemLaboratory Setup Mesenchymal stem cells dispersed within hydrogel constructs were exposed to alternating electric current using the laboratory setup depicted schematically (and not to scale) in FIG. 1. The system consists of a function generator, oscilloscope, multimeter, resistor, current-conducting base, current-conducting anode, a cathode substrate, and cell-culture chambers that are incorporated as part of an electric circuit. Incorporation of the cell-culture chambers as part of the electric circuit allows the mesenchymal stem cells contained within the cell-culture chambers to be exposed to alternating electric current for a specified duration and/or pattern of exposure in a sterile environment at constant temperature (e.g., 37° C.). A coaxial cable connected the positive output of the function generator to the positive end of a 1000-ohm-resistor and the negative output of the function generator to the current-conducting cathode substrate: this arrangement assured that the mesenchymal stem cells dispersed within the hydrogel constructs were exposed to electric current. To monitor the signal output from the function generator, a second coaxial cable connected the positive output of the oscilloscope to the positive end of the resistor and the negative output from the oscilloscope to the current-conducting cathode substrate. A multimeter read the alternating current (AC) voltage difference across the 1000-ohm-resistor.

Example 4

Mesenchymal Stem Cell Function Upon Exposure to Alternating Electric Current

Mesenchymal stem cell differentiation and other select functions pertinent to the formation of new bone at the cellular level were assessed and compared to responses of controls. that is, mesenchymal stem cells cultured under similar conditions but not exposed to alternating electric-current.
Assessment of MSC Viability Viability of mesenchymal stem cells was assessed after exposure to alternating electric current (a 10 Hz, sinusoidal wave at 10 or 40 microamperes for 6 hours per day as described in the Exposure of Human Mesenchymal Stem Cells to Alternating Electric Current in Vitro section) for 1, 7, and 14 consecutive days. For this purpose, a commercially mailable LIVE/DEAD viability/cytotoxicity assay was used. Under fluorescent microscopy, live cells appear green when excited at a 494 nm wavelength (517 nm emission), while dead cells appear red when excited at a 528 nm wavelength (617 nm emission). Cell viability was compared to results obtained from controls, i.e., cells cultured under similar culture conditions but not exposed to electric current.
Assessment of MSC Proliferation Mesenchymal stem cell proliferation was assessed for mesenchymal stem cells cultured in collagen hydrogel constructs (fabricated as described in the Fabrication of Cell-Containing Collagen Hydrogel Constructs section) in response to a sinusoidal. 10 Hz, either 10 or 40 µA, alternating electric-current for 6 hours per day (as described in the Exposure of Human Mesenchymal Stem Cells to Alternating Electric Current in Vitro sec(ion) after 1, 3, 7, 11 and 13 consecutive days of exposure to the alternating electric current. Each mesenchymal stem cell proliferation experiment was run in duplicate and repeated at three separate times.

Mesenchymal stem cell proliferation was determined using the Pico Green Assay, a fluorescent assay that quantifies the fluorescence of the DNA contained in the mesenchy mal stern cells present in the collagen hydrogel constructs and correlates this fluorescence to the DNA of a known number of cells. Mesenchymal stem cell number was determined from standard curves of fluorescence as a function of known numbers of mesenchy mal stem cells prepared and run in parallel with that from mesenchymal stem cells exposed to alternating electric current.

These results of mesenchymal stem cell proliferation were also compared to those obtained from controls, i.e., mesenchymal stem cells cultured under similar conditions but not exposed to alternating electric current.

Mesenchymal stem cell proliferation was reported as total cells per collagen hydrogel construct. Numerical data were statistically analyzed as described in the Analyses of Numerical Data section.
Assessment of MSC Differentiation Differentiation of mesenchymal stem cells in response to alternating electric current alone (that is, in the absence of biochemical factors such as dexamethasone or growth factors) was assessed through the determination of the expression profiles of select genes pertinent to mesenchymal stem cell differentiation (i.e., Runx-2, Osterix, Osteopontin, Osteocalcin, Collagen II, and Fatty Acid Binding Protein 4) using real-time reverse transcriptase polymerase chain reaction (RT-PCR). Gene expression of mesenchymal stem cells cultured in collagen hydrogel constructs and exposed to alternating electric current alone (that is, in the absence of biochemical factors such as dexamethasone or growth factors) were compared to profiles of the same genes expressed by mesenchymal stem cells cultured under similar conditions but not exposed to alternating electric current or biochemical factors (controls). Mesenchymal stem cell gene expression was reported as relative increase in expression (fold-change) above baseline (Day 0 mesenchymal stem cells). Numerical data were statistically analyzed as described in the Analyses of Numerical Data section.
Select Gene Expression of Mesenchymal Stem Cells Real time reverse transcriptase polymerase chain reaction (RT-PCR) was used as a means of quantifying the expression of select genes (namely, osterix, RUNX2, osteopontin, osteocalin) pertinent to osteoblast differentiation. Additionally, the expression of select genes pertinent to adipocyte differentiation (i.e., fatty acid binding protein 4; FABP4), and chondrocyte differentiation (i.e., Collagen II) were also investigated. Quantification of gene expression included: (i) RNA isolation, (ii) cDNA conversion, and (iii) RT-PCR analysis. Collagenase, an enzyme that selectively cleaves collagen chains, was used to digest collagen hydrogels and thus isolate the mesenchymal stem cells contained within. Collagenase was also used to lift MSC cultured on the two-dimensional. ITO-coated glass substrates.

Isolated mesenchymal stem cells were disrupted with TRIzol Reagent, a reagent designed to isolate high quality total RNA (as well as DNA and proteins) from cells. Chloroform was added to the TRIzol/cell solution and the resulting mixture separated into a lower red phenol-chloroform phase, an interphase. and a colorless upper aqueous phase. RNA was present exclusively in the aqueous phase. RNA from the aqueous phase was further cleaned to remove impurities using a RNAse kit in accordance with protocols supplied by the vendor. The cleaned RNA was then transcribed using a commercially available cDNA synthesis kit. This process resulted in cDNA, which was then amplified with specific primers for the genes of interest. Cyclophilin was used as a housekeeping gene to ensure equal loading of RNA into all RT-PCR reactions. Real time fluorescence measurements were recorded for each thermal cycle. The results obtained from mesenchymal stem cells exposed to alternating electric current were compared to those obtained from controls, i.e., cells cultured under similar conditions but not exposed to alternating electric current.
Assessment of the Synthesis and Release of Select Extracellular Matrix Proteins and Growth Factors Select proteins and growth factors pertinent to the composition of bone were determined in cell cultures exposed to alternating electric current. MSCs were: (i) released from collagen hydrogels (containing soluble chemical compounds secreted from the cells) using collagenase. and then (ii) lysed using a lysis buffer. For MSCs cultured on two-dimensional, ITO-coated glass substrates, MSCs were lysed from the substrate using a lysis buffer. MSC lysates were centrifuged to remove cell debris.

Extracted proteins and growth factors from MSC lysates were analyzed using gel electrophoresis. The resulting protein bands were visualized using an enhanced chemiluminescence detection kit and were semi-quantified using commercially available software.

Example 5

Analyses of Numerical Data

All numerical data were reported as mean±standard error of the mean. Data consisting of single comparisons were analyzed using the Student t-test, and data consisting of multiple comparisons were analyzed statistically according to standard analysis of variance (ANOVA) and Tukey's test. Outliers of real-time polymerase chain reaction data acquired from MSC gene expression studies and reported as "fold increase" above baseline were determined using the modified Z-score analysis technique; outlying data points (defined by a modified Z-score absolute value greater than 3.5) were excluded from further analysis. Values of p<0.05 indicated a statistically significant level of difference between the means of the experimental and respective control groups.

Example 6

The following is an example of how this technology can be used to preferentially differentiate MSCs to the osteoblast (but not to either chondrocyte or adipocyte) lineage when cultured within a three-dimensional matrix or scaffold in the absence of biochemical factors using either a 10 or 40 microampere alternating electric current at 10 Hertz for 6 hours per day for a period of several consecutive days.

Differentiation of adult human mesenchymal stem cells dispersed within type I collagen hydrogel constructs (initial seeding: 250,000 cells per gel) and exposed to a sinusoidal, 10 Hz, either 10 or 40 µA alternating electric current for 6 hours per day for 7 and 14 consecutive days in the absence of biochemical (such as dexamethasone and growth factors) was determined using RT-PCR analysis. As compared to controls, exposure to either 10 µA or 40 µA alternating electric current resulted in increased upregulation of osteocalcin (a late osteogenic gene) at day 14. whereas expression for all other osteogenic genes tested (specifically. Runx-2 and osterix (FIG. 2) and osteopontin (FIG. 3) was unaffected.

Figure 2:
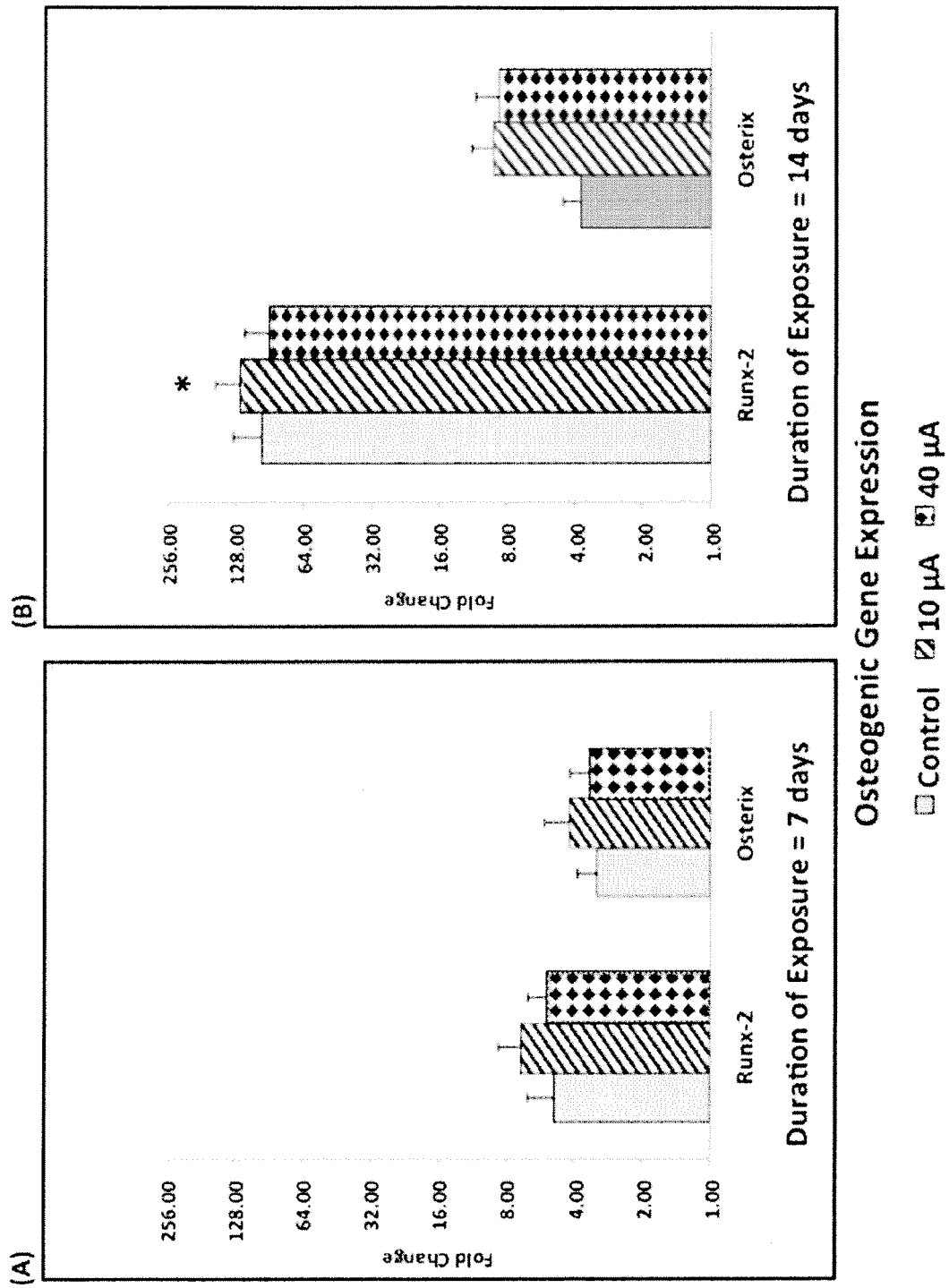
FIG. 2 is a graph showing that adult human mesenchymal stem cells cultured within type I collagen hydrogel constructs and exposed to either 10 or 40 µA alternating electric current for 6 hours daily for up to 14 consecutive days preferentially express genes indicative to the osteoblast phenotype. Runx-2, a pre-osteogenic gene, was significantly upregulated as a function of duration (14 versus 7 days, FIGS. 2(B) and 2(A), respectively) when MSCs were exposed to 10 µA alternating electric current. In contrast, the expression of Runx-2 at day 14 remained similar to that of day 7 when MSCs were cultured under control conditions, that is, not exposed to alternating electric current. Data are values±standard error of the mean; n=4*$p<0.05$ (ANOVA and Tukey's test: Runx-2 expression at day 14 as compared to Runx-2 expression at day 7 under 10 µA alternating electric current).

When comparing the expression of osteogenic genes by MSCs exposed to 10 µA alternating electric current for 6 hours daily as a function of duration of exposure (days), expression of Runx-2 (a pre-osteogenic gene: FIG. 2), osteopontin and osteocalcin (both late-osteogenic genes: FIG. 3) significantly increased at day 14 as compared to results obtained at day 7. Exposure of MSCs to 40 µA alternating electric current resulted in a significant increase in the expression of osteocalcin (FIG. 3(B)) at day 14 as compared to results obtained at day 7. In contrast, Runx-2, osterix, osteopontin, and osteocalcin gene expression by MSCs cultured under control conditions for either 7 or 14 consecutive days did not increase as a function of duration of exposure to alternating electric current.

Mesenchymal stem cells exposed to the alternating electric current levels tested for 7 and 14 consecutive days in the absence of biochemical compounds, such as dexamethasone and growth factors, did not express genes characteristic of either the adipogenic (specifically, Fatty Acid Binding Protein-4) or the chondrogenic (specifically, type II collagen) phenotypes.

Example 7

The following is an example of how this technology can be used to preferentially differentiate MSCs to the osteoblast (but not to either chondrocyte or adipocyte) lineage when cultured on a two-dimensional substrate in the absence of biochemical factors using either a 10 or 40 microampere alternating electric current at 10 Hertz for 6 hours per day.

Differentiation of adult human mesenchymal stem cells (initial seeding: 75,000 cells/cm$^2$) cultured on two-dimensional, ITO-glass substrates was determined after exposure to a sinusoidal, either 10 Hz, 10 or 40 µA alternating electric current for 6 hours per day for 7 consecutive days using Western Blot analysis.

Results demonstrated increased production of Runx-2 in the cell lysate of MSCs exposed to 10 µA of alternating electric current (FIG. 5); at this time, expression of Runx-2 in cell lysates of MSCs exposed to 40 µA of alternating electric current was similar to that of the respective controls (i.e., MSCs not exposed to alternating electric current).

Differentiation of adult human mesenchymal stem cells (initial seeding: 75,000 cells/cm$^2$) cultured on two-dimensional, ITO-glass substrates was determined after exposure to a sinusoidal, 10 Hz, either 10 or 40 µA alternating electric current for 6 hours per day for either 7 or 14 consecutive days using RT-PCR analysis.

Expression of select genes indicative of the pre-osteoblast (Runx-2) and of the late-osteoblast (osteopontin) differentiation stages showed an increasing trend of upregulation when MSCs were exposed to 10 alternating electric current for 7 days (FIG. 5 and FIG. 6, respectively)

In contrast, and as compared to respective controls. expression of Runx-2 was similar, but expression of osteopontin was increased when MSCs are exposed to 40 µA alternating electric current for 7 consecutive days (FIG. 5 and FIG. 6, respectively). At day 14, increased upregulation of Runx-2 (FIG. 5) and of osteopontin (FIG. 6) was observed after exposure of MSCs to 40 µA of alternating electric current as compared to respective controls.

Most importantly, gene expression of proteins pertinent to the adipogenic and chondrogenic differentiation pathways (i.e., Fatty Acid Binding Protein-4 and Collagen II, respectively) was not detected when mesenchymal stem cells were exposed to alternating electric current at the current level and duration of exposures tested.

REFERENCES CITED

The following references, to the extent that they provide exemplary procedural or other details supplementary to those set forth herein, are specifically incorporated herein by reference.

United States Pate Documents

United States Patent Publication US2011/0034753 published Feb. 10, 2011, with Dobson listed as the inventor.

United States Patent Publication US2008/0039901 published Feb. 14, 2008. with Kronberg, et al. listed as the inventors.

United States Patent Publication US2010/0233142 published Sep. 16, 2010, with McLaughlin, et al. listed as the inventors.

United States Patent Publication US2010/0233142 published Sep. 16, 2010, with McLaughlin, et al. listed as the inventors.

United States Patent Publication US2008/0227202 published Sep. 18, 2008, with Dancu listed as the inventor.

United States Patent Publication US2008/0227191 published Sep. 18, 2008, with Dancu listed as the inventor.

United States Patent Publication US2009/0124013 published May 14, 2009, with Kouns listed as the inventor.

What is claimed:

1. A method for directing, enhancing, and accelerating mesenchymal stem cell differentiation, comprising the steps of: culturing mesenchymal stem cells within a three dimensional matrix or scaffold; exposing mesenchymal stem cells to alternating electric current, wherein the alternating electric current is a current in the range from 10 µA to 40 µA.

2. The method of claim 1, wherein the mesenchymal stem cells are differentiated to either osteoblast or chondrocyte lineages.

3. The method of claim 1, wherein the mesenchymal stem cells are cultured within a three-dimensional matrix or scaffold.

4. The method of claim 3, wherein the three-dimensional matrix or scaffold is current-conducting.

5. The method of claim 1, wherein the three-dimensional matrix is a collagen hydrogel.

6. The method of claim 1, wherein the mesenchymal stem cells are cultured in two dimensions on a substrate.

7. The method of claim 6, wherein the substrate is current-conducting.

8. The method claim 6, wherein the substrate is Indium Tin Oxide-coated glass.

9. The method of claim 1, wherein the alternating electric current is a frequency of 10 Hz.

10. The method of claim 1, wherein the alternating electric of either a continuous or intermittent pattern and a duration of application of 6 hours per day for up to 28 consecutive days.

11. A method for directing, enhancing, and accelerating mesenchymal stem cell differentiation, comprising the steps of:
   culturing mesenchymal stem cells;
   exposing mesenchymal stem cells to alternating electric current wherein the alternating electric current is a frequency of 10 Hz.

12. The method of claim 11, wherein mesenchymal stem cells are differentiated to either osteoblast or chondrocyte lineages.

13. The method of claim 11, wherein the mesenchymal stem cells are cultured within a three-dimensional matrix or scaffold.

14. The method of claim 13, wherein the three-dimensional matrix or scaffold is current-conducting.

15. The method of claim 13, wherein the three-dimensional matrix is a collagen hydrogel.

16. The method of claim 11, wherein the alternating electric current is of either a continuous or intermittent pattern and a duration of application of 6 hours per day for up to 28 consecutive days.

17. The method of claim 11, wherein the mesenchymal stem cells are cultured in two dimensions on a substrate.

18. A method for directing, enhancing, and accelerating mesenchymal stem cell differentiation, comprising the steps of:
   culturing mesenchymal stem cells on a two dimensional substrate;
   exposing mesenchymal stem cells to alternating electric current, wherein the alternating electric current is of either a continuous or intermittent pattern and a duration of application of 6 hours per day for up to 28 consecutive days.

19. The method of claim 18, wherein the mesenchymal stem cells are differentiated to either osteoblast or chondrocyte lineages.

20. The method of claim 19, wherein the substrate is current-conducting.

21. The method of claim 19, wherein the substrate is Indium Tin Oxide-coated glass.

22. The method of claim 18, wherein the mesenchymal stem cells are cultured within a three-dimensional matrix or scaffold.

23. The method of claim 22, wherein the three-dimensional matrix or scaffold is current-conducting.

24. The method of claim 22, wherein the three-dimensional matrix is a collagen hydrogel.

25. The method of claim 18, wherein the mesenchymal stem cells are cultured in two dimensions on a substrate.

26. The method of claim 25, wherein the substrate is current-conducting.

27. The method of claim 25, wherein the substrate is Indium Tin Oxide-coated glass.

28. A method for directing, enhancing, and accelerating mesenchymal stem cell differentiation, comprising the steps of:
   culturing mesenchymal stem cells within a three-dimensional matrix or scaffold;
   exposing mesenchymal stem cells to alternating electric current; and wherein the alternating electric current is a current in the range from 10 µA to 40 µA.

29. A method for directing, enhancing, and accelerating mesenchymal stem cell differentiation, comprising the steps of:
   culturing mesenchymal stem cells within a three-dimensional matrix or scaffold;
   exposing mesenchymal stem cells to alternating electric current; and wherein the alternating electric current is a frequency of 10 Hz.

30. A method for directing, enhancing, and accelerating mesenchymal stem cell differentiation, comprising the steps of:
   culturing mesenchymal stem cells within a three-dimensional matrix or scaffold;
   exposing mesenchymal stem cells to alternating electric current; and wherein the alternating electric current is for either a continuous or intermittent pattern and a duration of application of 6 hours per day for up to 28 consecutive days.

31. A method for directing, enhancing, and accelerating mesenchymal stem cell differentiation, comprising the steps of:
   culturing mesenchymal stem cells in two dimensions on a substrate;
   exposing mesenchymal stem cells to alternating electric current; and wherein the alternating electric current is a current in the range from 10 µA to 40 µA.

32. A method for directing, enhancing, and accelerating mesenchymal stem cell differentiation, comprising the steps of:
   culturing mesenchymal stem cells in two dimensions on a substrate;
   exposing mesenchymal stem cells to alternating electric current; and wherein the alternating electric current is a frequency of 10 Hz.

33. A method for directing, enhancing, and accelerating mesenchymal stem cell differentiation, comprising the steps of:
   culturing mesenchymal stem cells on a two-dimensional substrate;
   exposing mesenchymal stem cells to alternating electric current; and wherein the alternating electric current is of either a continuous or intermittent pattern and a duration of application of 6 hours per day for up to 28 consecutive days.

* * * * *